US00PP28810P3

(12) United States Plant Patent
van den Haak

(10) Patent No.: US PP28,810 P3
(45) Date of Patent: Dec. 26, 2017

(54) ***PHLOX* PLANT NAMED 'APPOFAMWE'**

(50) Latin Name: *Phlox paniculata*
Varietal Denomination: Appofamwe

(71) Applicant: Jelle van den Haak, Amsterdam (NL)

(72) Inventor: Jelle van den Haak, Amsterdam (NL)

(73) Assignee: Gootjes—Allplant B.V., Schagen (NL)

( * ) Notice: Subject to any disclaimer, the term of this patent is extended or adjusted under 35 U.S.C. 154(b) by 32 days.

(21) Appl. No.: 14/999,215

(22) Filed: Apr. 11, 2016

(65) Prior Publication Data

US 2017/0295696 P1 Oct. 12, 2017

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Susan McCormick Ewoldt
(74) *Attorney, Agent, or Firm* — C. A. Whealy

(57) ABSTRACT

A new and distinct cultivar of *Phlox* plant named 'Appofamwe', characterized by its broadly upright and relatively compact plant habit; dark green-colored leaves; freely flowering habit, numerous large white-colored flowers with red purple-colored centers; long flowering period; and good garden performance.

2 Drawing Sheets

Botanical designation: *Phlox paniculata.*
Cultivar denomination: 'APPOFAMWE'.

BACKGROUND OF THE INVENTION

The present invention relates to a new and distinct cultivar of *Phlox* plant, botanically known as *Phlox paniculata* and hereinafter referred to by the name 'Appofamwe'.

The new *Phlox* plant is a product of a planned breeding program conducted by the Inventor in Andijk and Hazerswoude-Dorp, The Netherlands. The objective of the breeding program was to create new compact and vigorous *Phlox* plants with numerous large flowers.

The new *Phlox* plant originated from an open-pollination in August, 2009 in Andijk, The Netherlands, of an unnamed proprietary selection of *Phlox paniculata*, not patented, as the female, or seed, parent, with an unknown selection of *Phlox paniculata* as the male, or pollen, parent. The new *Phlox* plant was discovered and selected by the Inventor as a single flowering plant from within the progeny of the stated open-pollination in a controlled environment in Hazerswoude-Dorp, The Netherlands in August, 2013.

Asexual reproduction of the new *Phlox* plant by terminal cuttings in a controlled greenhouse environment in Andijk, The Netherlands since 2014 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Appofamwe'. These characteristics in combination distinguish 'Appofamwe' as a new and distinct *Phlox* plant:

1. Broadly upright and relatively compact plant habit.
2. Dark green-colored leaves.
3. Freely flowering habit, numerous large white-colored flowers with red purple-colored centers.
4. Long flowering period.
5. Good garden performance.

Plants of the new *Phlox* and the female parent selection differ primarily in growth habit as plants of the new *Phlox* are more uniform than plants of the female parent selection.

Plants of the new *Phlox* can also be compared to plants of *Phlox paniculata* 'Barsixty', disclosed in U.S. Plant Pat. No. 22,211. In side-by-side comparisons, plants of the new *Phlox* and 'Barsixty' differ in the following characteristics:

1. Plants of the new *Phlox* are more vigorous than plants of 'Barsixty'.
2. Plants of the new *Phlox* and 'Barsixty' differ in leaf color as plants of 'Barsixty' have lighter green-colored leaves.
3. Plants of the new *Phlox* have slightly larger flowers than plants of 'Barsixty'.
4. Plants of the new *Phlox* and 'Barsixty' differ in flower color as plants of 'Barsixty' have flowers with darker-colored centers.

BRIEF DESCRIPTION OF THE PHOTOGRAPHS

The accompanying photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet is a side perspective view of a typical flowering plant of 'Appofamwe' grown in a container.

The photograph on the second sheet is a close-up view of a typical flowering plant of 'Appofamwe'.

DETAILED BOTANICAL DESCRIPTION

The aforementioned photographs and following observations and measurements describe plants grown during the summer in 15-cm containers in an outdoor nursery in Mijdrecht, The Netherlands and under cultural practices typically used in commercial *Phlox* production. During the production of the plants, day temperatures ranged from 15° C. to 28° C. and night temperatures ranged from 10° C. to 18° C. Plants were pinched five weeks after planting and were 19 weeks old when the photographs and description were taken. In the following description, color references are made to The Royal Horticultural Society Colour Chart, 2015 Edition, except where general terms of ordinary dictionary significance are used.

Botanical classification: *Phlox paniculata* 'Appofamwe'.

Parentage:

*Female, or seed, parent*.—Unnamed proprietary selection of *Phlox paniculata*, not patented.

*Male, or pollen, parent*.—Unknown selection of *Phlox paniculata*, not patented.

Propagation:

*Type*.—By terminal cuttings.

*Time to initiate roots, summer*.—About 12 days at temperatures about 20° C.

*Time to initiate roots, winter*.—About 16 days at temperatures about 20° C.

*Time to produce a rooted young plant, summer*.—About 36 days at temperatures about 18° C.

*Time to produce a rooted young plant, winter*.—About 42 days at temperatures about 18° C.

*Root description*.—Medium in thickness, fleshy; typically white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Herbaceous perennial; broadly upright and relatively compact plant habit; overall shape, broadly obovate; low vigor to moderately vigorous in growth habit.

*Plant height*.—About 36 cm.

*Plant width* (*spread*).—About 37.9 cm.

*Lateral branches*.—Quantity: About eight primary lateral branches per plant. Length: About 23.8 cm. Diameter: About 4 mm. Internode length: About 2.6 cm. Strength: Strong. Aspect: Upright to about 35° from vertical. Texture and luster: Smooth, glabrous; slightly glossy. Color: Close to 144B.

Leaf description:

*Arrangement*.—Opposite, simple.

*Length*.—About 10.2 cm.

*Width*.—About 3.3 cm.

*Shape*.—Elliptic; slightly carinate.

*Apex*.—Apiculate.

*Base*.—Truncate.

*Margin*.—Entire; very finely serrate, inconspicious.

*Texture and luster, upper and lower surfaces*.—Sparsely pubescent; slightly rugose and slightly rough; slightly glossy.

*Venation pattern*.—Pinnate.

*Color*.—Developing leaves, upper surface: Close to 143A. Developing leaves, lower surface: Close to 143C. Fully expanded leaves, upper surface: Close to NN137B; venation, close to 144A to 144B. Fully expanded leaves, lower surface: Close to between 146B and 147B; venation, close to 144B.

*Petioles*.—Length: About 3 mm. Diameter: About 2 mm by 2.5 mm. Texture, upper and lower surfaces: Smooth, glabrous. Color, upper and lower surfaces: Close to 144B.

Flower description:

*Flower type and flowering habit*.—Single rotate and salverform flowers arranged in compound terminal panicles; flowers face upright to outwardly; panicles roughly hemispherical in shape; freely flowering habit with about 150 flowers developing per inflorescence and about 1,200 flowers developing per plant during the flowering season.

*Fragrance*.—Moderately fragrant; sweet, pleasant.

*Natural flowering season*.—Plants begin flowering about nine months after planting; long flowering period, plants flower continuously from July through September in The Netherlands.

*Flower longevity*.—Flowers last about ten days on the plant; flowers not persistent.

*Flower buds*.—Height: About 2.6 cm. Diameter: About 4 mm. Shape: Narrowly elliptic. Color: Close to 75C to 75D; developing tube, close to N77D; developing calyx, close to 145B, towards the apex, strongly tinged with close to 200C.

*Inflorescence height*.—About 13.7 cm.

*Inflorescence diameter*.—About 14.1 cm.

*Flower diameter*.—About 3.5 cm.

*Flower depth*.—About 2.5 cm.

*Petals*.—Quantity per flower: Typically five in a single whorl; petals fused at the base into a narrow tube; free parts touching to slightly imbricate. Length: Overall, about 3.7 cm; lower fused portion, about 2.1 cm. Lobe width: About 1.6 cm. Shape: Free part, spatulate. Apex: Straight to broadly rounded and shallowly emarginate. Margin: Entire. Texture and luster, upper surface: Smooth, glabrous; moderately velvety; matte. Texture and luster, lower surface: Smooth, glabrous; slightly velvety; slightly glossy. Color: When opening, upper surface: Close to NN155D; towards the throat, close to N74A; throat, close to N77B. When opening, lower surface: Close to NN155C; towards the tube, close to 75C; tube, close to N77B. Fully opened, upper surface: Close to NN155D; towards the throat, close to NN74B; throat, close to N77B; with development, color becoming closer to NN155C, towards the throat, slightly tinged with close to NN74D and throat, close to 76C. Fully opened, lower surface: Close to NN155C; towards the tube, close to 75C; tube, close to N77B.

*Sepals*.—Quantity per flower: Typically five in a single whorl, fused towards the base; calyx, campanulate. Length: About 1 cm. Width: About 1 mm. Shape: Lanceolate. Apex: Narrowly apiculate. Margin: Entire. Texture and luster, upper and lower surfaces: Smooth, glabrous; slightly glossy. Color: When opening and fully opened, upper surface: Close to 144B. When opening and fully opened, lower surface: Close to 145B; towards the apex, strongly tinged with close to 200C.

*Peduncles*.—Length, primary peduncles: About 10.8 cm. Diameter, primary peduncles: About 3 mm. Length, secondary peduncles: About 5.6 cm. Diameter, secondary peduncles: About 1.5 mm. Aspect, primary peduncles: Erect. Aspect, secondary peduncles: About 35° from vertical. Strength: Strong. Texture: Smooth, glabrous. Color: Close to 144B.

*Pedicels*.—Length: About 5 mm. Diameter: About 1 mm. Angle: About 40° from the peduncle axis. Strength: Strong. Texture: Smooth, glabrous. Color: Close to 144B.

*Reproductive organs*.—Stamens: Quantity per flower: Typically five; filaments fused with petals. Filament length: About 1 mm. Filament color: Close to 155A. Anther length: About 2 mm. Anther shape: Oblong; basifixed. Anther color: Close to 160C. Pollen amount: Scarce to moderate. Pollen color: Close to 158D. Pistils: Quantity per flower: One. Pistil length: About 1.9 cm. Stigma shape: Cleft, three-parted. Stigma color: Close to 150D. Style length: About 1.8 cm. Style color: Close to N77C. Ovary color: Close to 143B.

*Seeds and fruits*.—Seed and fruit development have not been observed on plants of the new *Phlox*.

Garden performance: Plants of the new *Phlox* have been observed to have good garden performance and tolerate rain, wind, high temperatures about 35° C. and to be winter hardy to USDA Hardiness Zone 6.

Pathogen & pest resistance: Plants of the new *Phlox* have been not been observed to be resistant to pathogens and pests common to *Phlox* plants.

It is claimed:

1. A new and distinct *Phlox* plant named 'Appofamwe' as illustrated and described.

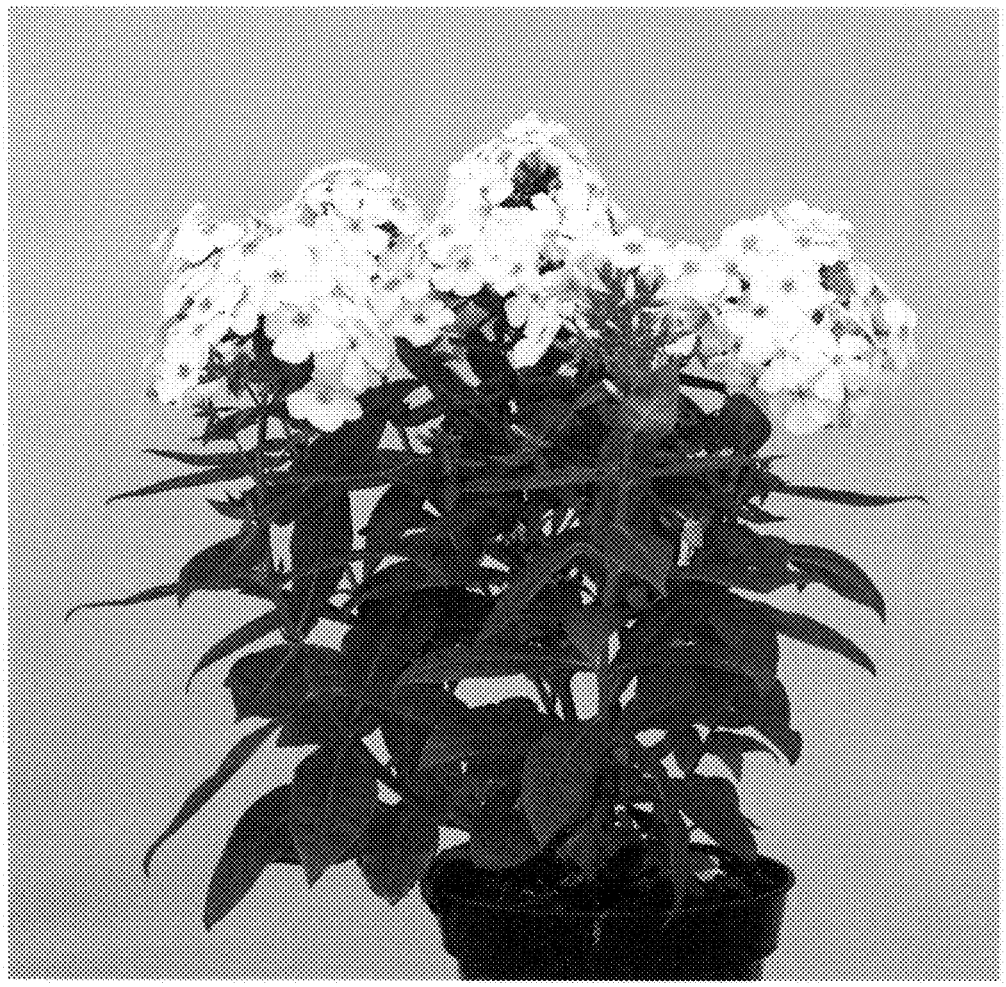

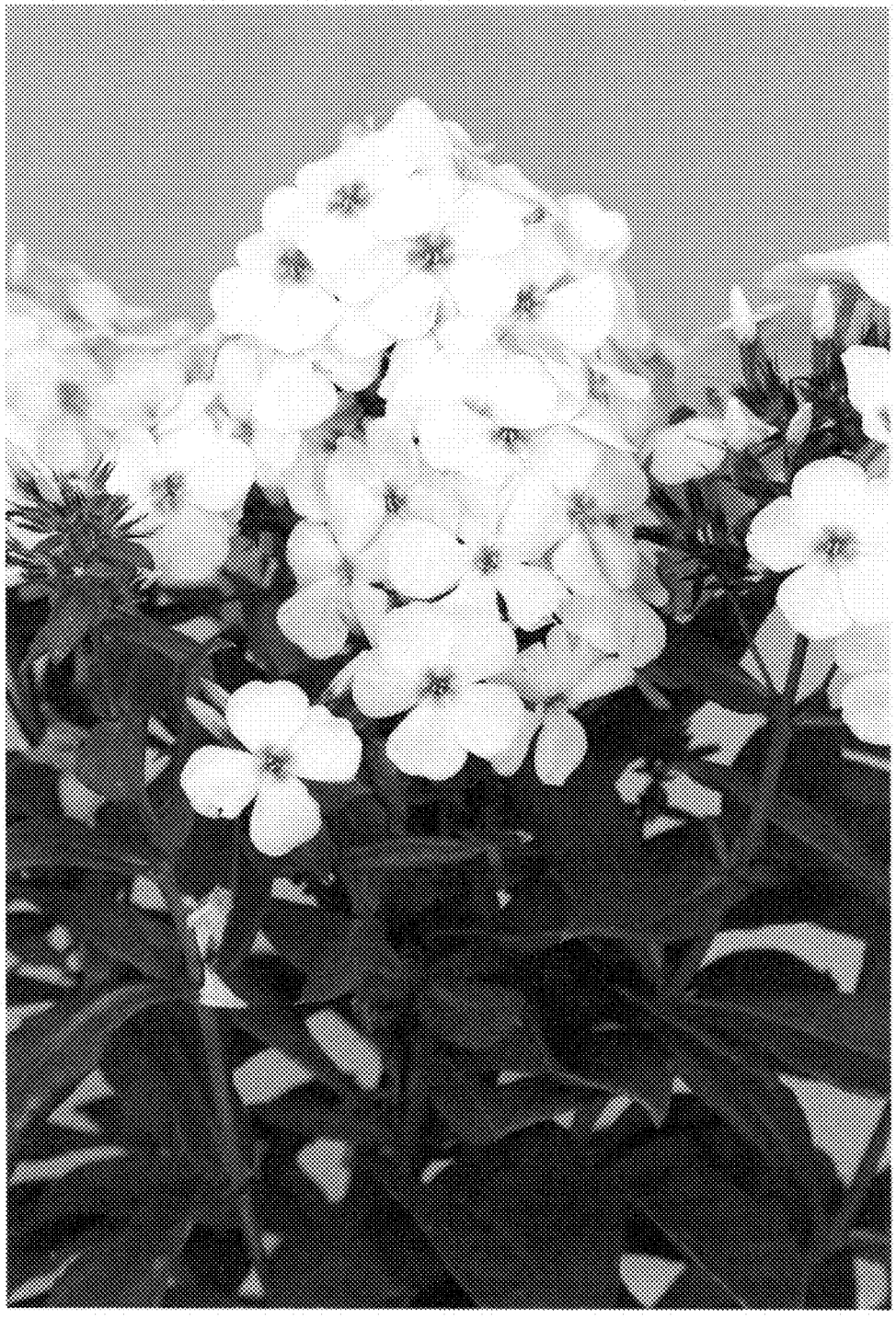

* * * * *